United States Patent [19]

Bradley

[11] 4,337,157
[45] Jun. 29, 1982

[54] BIOPOLYMER FILTRATION PROCESS

[75] Inventor: Timothy G. Bradley, Littleton, Colo.

[73] Assignee: Manville Service Corporation, Denver, Colo.

[21] Appl. No.: 887,573

[22] Filed: Mar. 17, 1978

[51] Int. Cl.³ .............................................. B01D 15/00
[52] U.S. Cl. ..................................... 210/691; 210/807
[58] Field of Search .................. 195/31 P; 210/24, 39, 210/40, 41, 65, 75, 691, 807; 423/331, 635; 536/1

[56] References Cited

U.S. PATENT DOCUMENTS

| | | | |
|---|---|---|---|
| 2,539,397 | 1/1951 | Bottoms et al. | 423/331 |
| 3,208,526 | 9/1965 | Patton et al. | 195/31 P |
| 3,711,462 | 1/1973 | Abdo | 536/1 |

OTHER PUBLICATIONS

"Enhanced Recovery of Oil and Gas", U.S.D.O.E. Brochure OPA-009 (1977).
"Micellar–Polymer Injection System has Special Features", *Oil & Gas Journal*, pp. 79–85 (Oct. 3, 1977).
Lipton, "Improved Injectability of Biopolymer Solutions", Soc. of Petroleum Engineers paper SPE 5009 (Denver, Colorado, Apr. 1975).
Yost et al., "Filtration of Polymer Solutions", Soc. of Petroleum Engineers paper SPE 4746 (Tulsa, Oklahoma, Apr. 1974).

*Primary Examiner*—Ivars C. Cintins
*Attorney, Agent, or Firm*—Robert M. Krone; Joseph J. Kelly

[57] ABSTRACT

A process for the filtration of biopolymer solutions is described, comprising contacting a biopolymer solution with an adsorbent material having a pH in the range of 8.5 to 10.0, preferably for a period of about 15 minutes. Synthetic calcium silicate and magnesium oxide are the preferred contacting materials.

3 Claims, 4 Drawing Figures

BIOPOLYMER FILTRATION PROCESS

BACKGROUND OF THE INVENTION

The invention herein relates to filtration processes. More particularly it relates to processes for filtering biopolymers.

In tertiary oil recovery processes it is conventional to use polymeric materials in the flooding solution which is pumped through the oil-bearing formation to scavenge oil from the rock. Commonly the two types of polymers used are polyacrylamides and biopolymers. Biopolymers are preferred over the polyacrylamides because during the recovery process the polymer solution must be pumped at high pressure and high shear rates through the formation, and the polyacrylamides are much more shear sensitive than are the biopolymers. Biopolymers, however, have the disadvantage that they can cause wellbore impairment due to the presence of unhydrated biopolymer material and/or bacterial debris. Thus, in order for biopolymers to be successfully used in tertiary oil recovery they must be subjected to filtration to remove the unhydrated biopolymer material and the bacterial debris which is present.

Filtration of these components, particularly the bacterial debris, has in the past proved to be exceedingly difficult. The bacterial debris particles are quite small in size (usually on the order of 1 to 2 microns), are commonly coated with bipolymer, and have tendency to act as deformable solids. Further, since the viscosity of a biopolymer solution is higher than that of water the concentration of the filterable solution is limited.

It has been known in the past that subjecting biopolymer solutions to an alkaline environment would materially aid the filterability of the solution. Thus, washing of the polymer solution with an alkaline wash produces some improvement in the filterability of the polymer. However, cycle times (the period of time starting with the beginning of filtration and ending when the filter has become sufficiently clogged to raise the required filter pressure to an undesirable or otherwise predetermined level) are often still quite short and only small amounts of material can be filtered before the filter cycle ends. Further, elaborate processing equipment is required to meter the alkaline wash into the biopolymer solution, and maintenance of correct pH during filtration is difficult.

Diatomite filtration has been used with some degree of success in the past. However, neutral pH diatomites require the supplemental use of an alkaline component to obtain the correct pH. Alkaline diatomites are commonly too coarse to filter the small bacterial debris effectively. Similarly, adsorbent materials have been considered for biopolymer filtration, but these have the disadvantage that they remove desirable materials as well as undesirable materials.

It would thus be advantageous to have a biopolymer filtration process which utilizes solid filtration materials but which is selective to remove substantially only the undesirable components of the biopolymer solution, and which provides a correct and stable pH environment without the need for elaborate equipment and/or controls or use of supplemental materials.

BRIEF SUMMARY OF THE INVENTION

The invention herein is a process for the filtration of biopolymers which comprises contacting a liquid solution of biopolymers with a solid particulate adsorbent material which has a pH in the range of from 8.5 to 10.0. The invention also is a process for the filtration of biopolymers which comprises contacting a biopolymer solution with magnesia or synthetic calcium silicate in granular form for a period of about 15 minutes. It is preferred that the contact time be in the range of 15 to 30 minutes. The filtration material may be used as either a filter precoat or as a body feed, although the latter is preferred.

BRIEF DESCRIPTION OF THE DRAWINGS

The graphs of

DETAILED DESCRIPTION AND PREFERRED EMBODIMENTS

Figure 1:
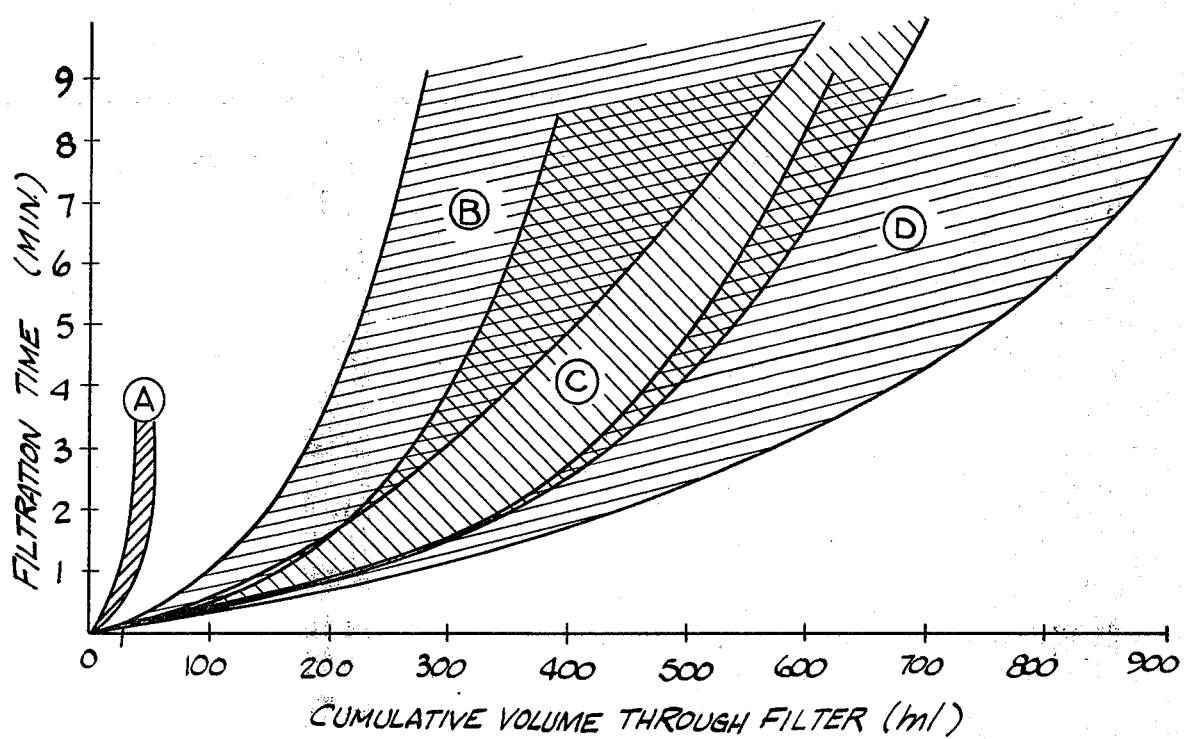
FIGS. 1 and 2 are plots of filter time versus cumulative volume through the filter and compare the efficiency of the present process with that of the prior art processes (FIG. 1) and compare synthetic calcium silicate usage at different concentrations and in different combinations with neutral filter aid (FIG. 2).

The invention herein is a process for the filtration of biopolymers of the type useful in tertiary oil recovery. These are generally bacteria of the group known as gram negative aerobic rods and cocci. Specifically, they are genera within three families: Pseudomonadaceae, Azotobacteraceae and Rhizobiaceae. Within the family Pseudomonadaceae the particular genera of interest are: Pseudomanas, Xanthomonas, Zoogloea and Glconobacter. Within the family Azotobacteraceae the genera of interest are: Azotobacter, Azomonas, Beijerinckia and Derxia. Within the family Rhizobiaceae the genera of interest are: Rhizobium and Agrobacterium. Of most importance is the bacteria of the species campestris of the genus Xanthomonas from which commercial biopolymers are all presently being made. For the purposes of this invention the solution of biopolymer may be a concentrated solution (on the order of 6000 ppm of biopolymer), which includes such materials as fermentation broths, or a diluted solution with a polymer concentration on the order of 300 ppm. Of course anything in the range between these values is suitable for the process and the solution may also be somewhat more dilute or more concentrated if desired. Acceptable concentrations may be determined by reference to conventional diatomite filtration, for materials which are filterable with diatomite will also be filterable with the high pH materials of the present invention. In general the practical limitation will be that the solution cannot be so concentrated in biopolymer that its viscosity prevents efficient filtration, nor should it be so dilute that excessive quantities of solution must be pumped through the filter for unduly long periods in order to obtain reasonable amounts of filtered material.

The solid granular or particulate adsorbent materials used as the filtration material will be those inorganic materials, primarily silicates and/or oxides, which have pH's of 8.5 to 10.0. Materials with pH's below 8.5 are not effective in this process, and those with pH's above 10.0 will degrade the biopolymer. Two materials which are useful in the present invention are synthetic calcium silicate and magnesium oxide (magnesia). Magnesium oxide of suitable purity is available from several commercial sources. Synthetic calcium silicates are available under the Trademark MICROCEL from Johns-Manville Corporation. Several grades of the latter are available each having a lime:silica ratio on the order of 1:2 and a pH in the range of from about 9.0 to about 9.8 in a 10% water slurry. These materials are available with particle sizes of at least about 97%-325 mesh (-44 microns) and surface areas of from about 80 to about 175 m²/g with specific gravities of aproximately 2.2 to 2.5. Small amounts (not exceeding about 6%) of oxides other than silica and lime, such as alumina, iron oxide, magnesia and alkali oxides are usually present in the synthetic materials. While magnesia and particularly the synthetic calcium silicates have specifically been found to be useful in the present invention, it is believed that other oxides and silicates with similar pH properties would also be suitable for use in this invention.

While the exact filtration mechanism occurring in the present inventon is not known, it is believed that the alkaline adsorbents provide a generally uniform and controlled alkaline pH which causes separation of the biopolymer from the unhydrated biopolymer and/or bacterial debris and allows the unhydrated material and the debris to act as small rigid solid particles which are removed from the solution by a combination of filtration and adsorption. While the two preferred materials (magnesia and synthetic calcium silicate) are known as adsorbents for some purposes, it appears that their action in the present process differs significantly from conventional adsorption since the concentration of biopolymer remains virtually unchanged, indicating that it is not being adsorbed on the inorganic material. Consequently, to the extent that the inorganic material may serve as an adsorbent it is apparently acting as a selective adsorbent for only the unhydrated polymer and the bacterial debris. This of course represents a significant improvement over conventional adsorbent processes which indiscriminately remove biopolymer along with the undesired material.

In the filtration process of the present invention the inorganic material may be present as either a filter precoat, a body feed or both. Further, different materials may be used as body feed and precoat. It is preferable that the inorganic material of the present invention be used as a body feed either alone or in conjunction with a precoat of inorganic material of this invention or another material which does not have the active properties and high pH of the present invention. Typical examples include the use of synthetic calcium silicate as a body feed either in connection with a precoat of synthetic calcium silicate or a precoat of another type of material such as diatomite which would not be particularly effective on its own.

Contact times may be varied according to choice, with consideration for both sufficient time to get good separation of the biopolymer from the unwanted unhydrated polymer and bacterial debris as well as economical contact time. It has been found that a contact time on the order of 15 to 30 minutes of contact time is adequate to obtain significant filtration. Other filtration parameters such as pressure, temperature and the like also are not critical and may be adjusted as desired within the limits of the equipment being used. Normally these will be substantially the same as filtration condition used for diatomite filtration. Parameters must be controlled such that the biopolymers are not subjected to undue temperature degradation and with the understanding that at higher temperatures the reaction mechanism which separates the biopolymer from the unhydrated polymer and bacterial debris in the alkaline environment can be expected to proceed more rapidly. Those skilled in the art will be aware of these various factors and can readily adjust the operating conditions of any given system accordingly to obtain the optimum degree of filtration.

Figure 2:
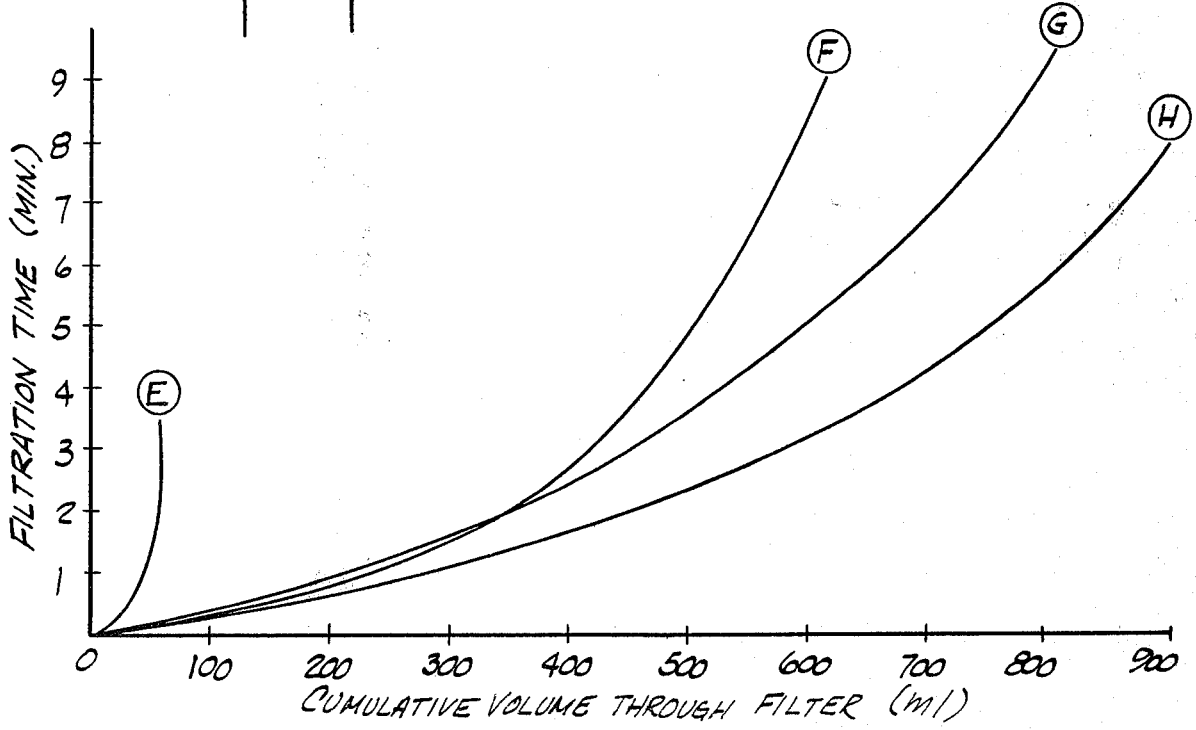

The various graphs presented show the superiority of this invention over those techniques used by the prior art. FIGS. 1 and 2 show the improved degree of filtration obtained with the present process as compared to prior art processes. In each case the biopolymer solution was filtered and a sample of the filtrate taken. This sample was then filtered through a 25 mm 0.8 micron membrane at a pressure of 20 psig for a period of 9 minutes. The more filtrate volume that passed through the membrane filter in this time, the cleaner the filtrate, and thus the more efficient the filtration. In FIG. 1 the four zones represent typical data of the various kinds of filtration used for biopolymer filtration. Zone A represents (1) filtration with no treating of the polymer and (2) filtration using simple alkali stripping of the polymer. Zone B represents filtration using neutral diatomite as the filter aid but no alkali stripping. Zone C represents (1) the two-step technique of first alkali stripping the solution and then filtering the stripped solution through diatomite and (2) enzyme digestion of the solution with or without diatomite filration. Zone D represents the process of this invention. Only the prior processes which utilized the time consuming and complex processes of stripping or enzyme digestion in one stage and diatomite filtration in another have the capability of operating as effectively as the present process. Even then it is clear from FIG. 1 that only prior art enzyme digestion/alkali stripping and diatomite processes which operate at maximum efficiency have the capability, and even then they are just barely equal to the present precess operating at minimum efficiency.

FIG. 2 shows individual examples in which the initial filtrations (from which the test filtrate samples were taken) were conducted with 500 pm of synthetic calcium silicate with pH 9.8 in the stock solution and 300 ppm of diatomite with pH of 7.0 as body feed (line F), 700 ppm of the same synthetic calcium silicate in the stock solution and 350 ppm of the same diatomite in the body feed (line G) and 350 ppm of the same synthetic calcium silicate as body feed with no diatomite present (line H). Also shown for comparison (line E) is a plot of the filtration of untreated biopolymer. In each case the test sample was diluted to a concentration of 300 ppm of the commercial biopolymer described above.

Figure 3:
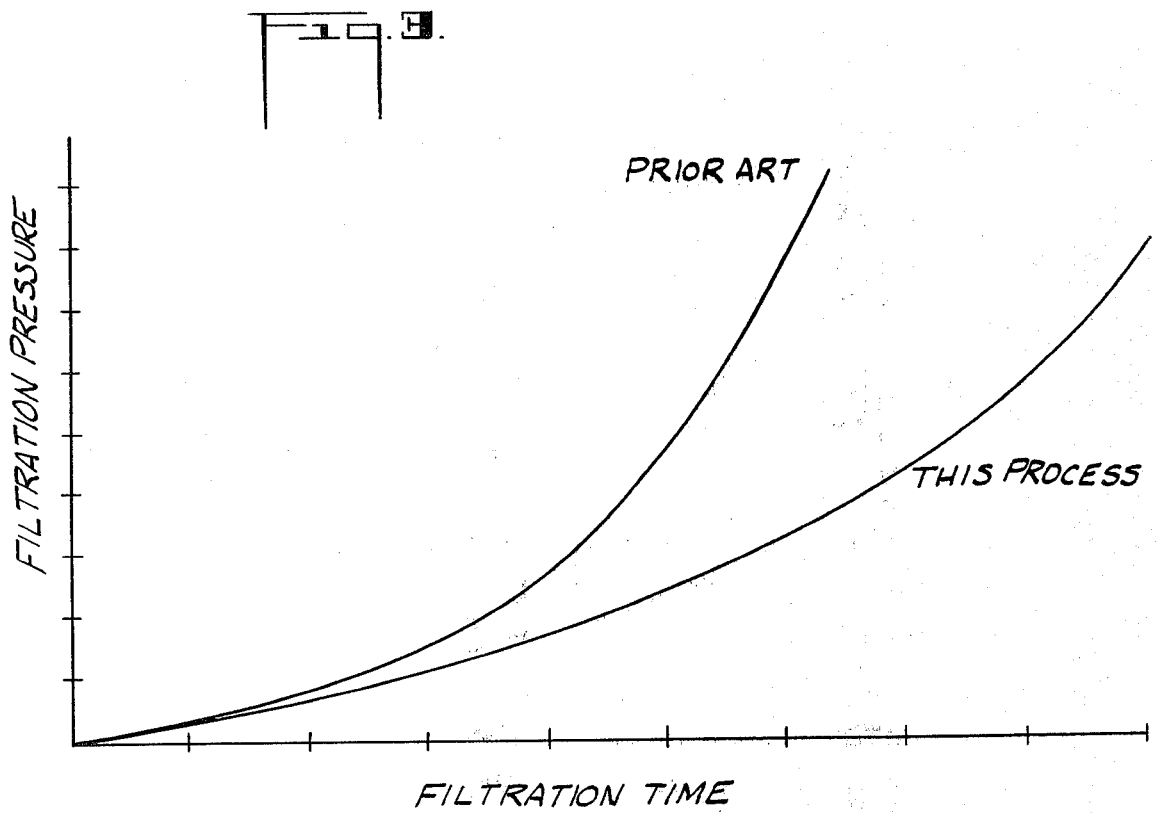
FIG. 3 is a generalized graph showing the improved cycle time of the present process.

In FIG. 3 a typical cycle time of the best prior art technique (alkali stripping pretreatment and diatomite filtration using 350 ppm of the diatomite described above as a body feed) is compared with a typical cycle time of a filtration run of the process of this invention (the particular run shown is that designated "Line H" in FIG. 2). It will be immediately evident that the preferred filtration technique of the present invention results in a cycle time increase of approximately 50%.

Figure 4:
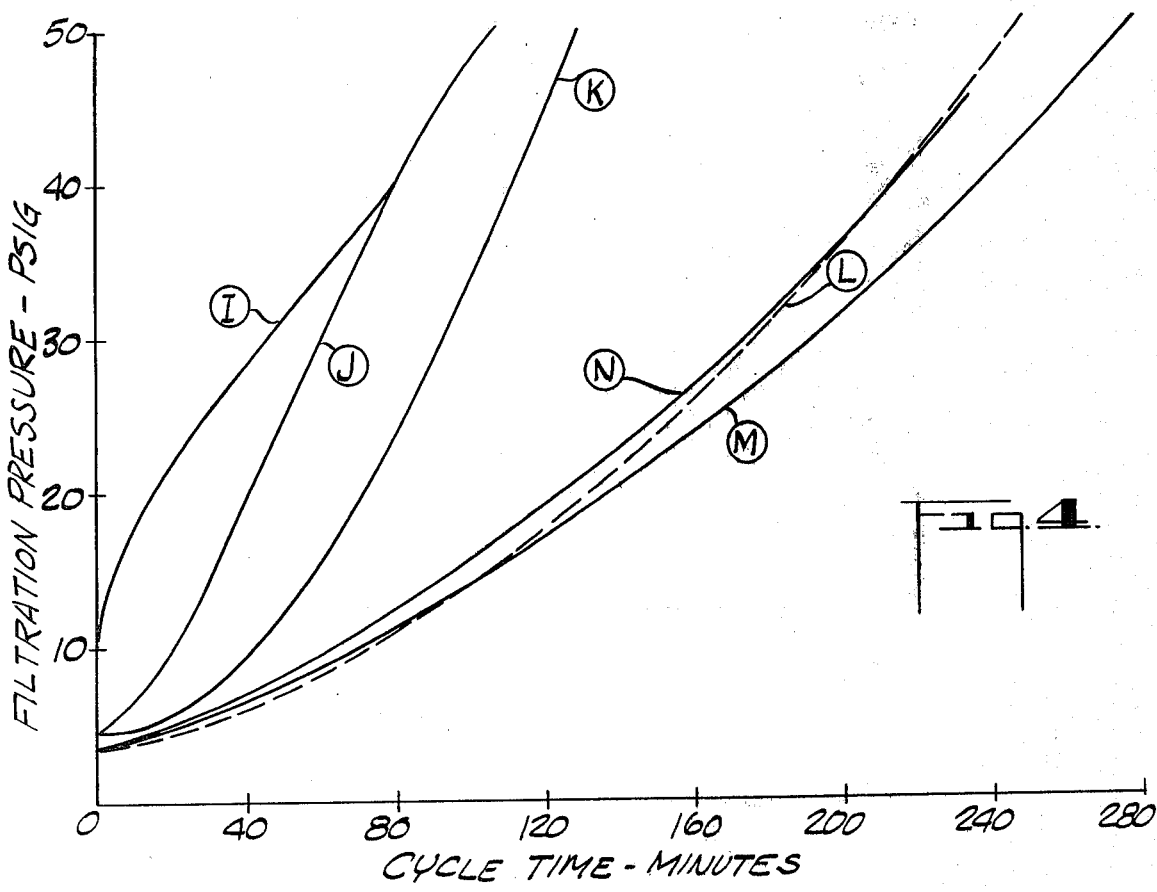
FIG. 4 is a graph comparing cycle times of the present process and several types of prior art processes.

FIG. 4 shows in more detail typical cycle times (defined here as time from start of filtration to time to reach 50 psig filter pressure—with the exceptions that Run I was terminated at 40 psig and that in Run N the quantity of test sample was exhausted before 50 psig pressure was reached so the run terminated at 46 psig). The details of each run (all of which used 300 ppm biopolymer) are listed in the Table below.

| Filtration | | | Quantity | | Biopolymer Feed |
| --- | --- | --- | --- | --- | --- |
| Run | Material | pH | ppm | Use | Pretreatment |
| I | diatomite | 7.0 | 300 | as body feed | none |
| J | diatomite | 7.0 | 750 | as body feed | none |
| K | diatomite | 7.0 | 750 | as body feed | enzyme digestion |
| L | diatomite | 7.0 | 350 | as body feed | alkali stripping |
| M | S.C.S.(a) | 9.8 | 500 | in stock solution | (b) |
| N | S.C.S.(a) | 9.8 | 700 | in stock solution | (b) |

(a) Synthetic calcium silicate
(b) 300 ppm diatomite (pH = 7.0) as body feed

It will immediately be evident that only the best (and most complicated) of the prior art processes is as effective as the present (simplified) process.

The improved and simplified filtration is reflected in many aspects. The process of this invention permits the use of smaller filter area or improved economics per unit of filtered material and longer filter cycles. There is also a decrease in the ratio of down time to onstream time. In addition the entire process is substantially simplified as compared to the prior art two-step processes.

What is claimed is:

1. A process for the filtration of biopolymers for the removal of unhydrated biopolymer material and bacterial debris which comprises contacting a liquid solution of biopolymers with a solid granular adsorbent material have a pH of 8.5 to 10.0 wherein said solid granular adsorbent material is selected from the group consisting of magnesia and synthetic calcium silicate.

2. A process as in claim 1 wherein said contacting is for a period of about 15 to 30 minutes.

3. A process as in claim 1 wherein said material is synthetic calcium silicate.

* * * * *